U S010767357B2

(12) United States Patent
Kazes

(10) Patent No.: US 10,767,357 B2
(45) Date of Patent: Sep. 8, 2020

(54) SANITATION APPARATUS AND METHOD

(71) Applicant: Erez Kazes, Hertzelia (IL)

(72) Inventor: Erez Kazes, Hertzelia (IL)

( * ) Notice: Subject to any disclaimer, the term of this patent is extended or adjusted under 35 U.S.C. 154(b) by 0 days.

(21) Appl. No.: 16/499,842

(22) PCT Filed: Apr. 30, 2018

(86) PCT No.: PCT/IL2018/050474
§ 371 (c)(1),
(2) Date: Jan. 6, 2020

(87) PCT Pub. No.: WO2018/203330
PCT Pub. Date: Nov. 8, 2018

(65) Prior Publication Data
US 2020/0173156 A1    Jun. 4, 2020

Related U.S. Application Data

(60) Provisional application No. 62/492,971, filed on May 2, 2017, provisional application No. 62/661,674, filed on Apr. 24, 2018.

(51) Int. Cl.
*E03D 9/00* (2006.01)
*E03D 9/052* (2006.01)
*B65D 83/26* (2006.01)
*A61L 9/20* (2006.01)
*A61L 9/14* (2006.01)

(52) U.S. Cl.
CPC .............. *E03D 9/005* (2013.01); *A61L 9/145* (2013.01); *A61L 9/20* (2013.01); *B65D 83/262* (2013.01); *E03D 9/052* (2013.01); *A61L 2209/111* (2013.01); *A61L 2209/12* (2013.01); *A61L 2209/134* (2013.01)

(58) Field of Classification Search
CPC ....................................... E03D 9/005
USPC ........................................... 4/348
See application file for complete search history.

(56) References Cited

U.S. PATENT DOCUMENTS

2007/0256226 A1    11/2007   Pinizzotto
2009/0249533 A1    10/2009   Sawalski et al.
2012/0266920 A1    10/2012   Burt et al.

*Primary Examiner* — Lori L Baker

(57) ABSTRACT

A toilet bowl sanitizer includes a flush activated sprayer. The sprayer creates a barrier for contaminants from leaving the toilet bowl.

23 Claims, 7 Drawing Sheets

SANITATION APPARATUS AND METHOD

CROSS REFERENCES TO RELATED APPLICATIONS

This application is related to and claims priority from commonly owned U.S. Provisional Patent Application Ser. No. 62/661,674, entitled: Sanitation Apparatus and Method, filed on Apr. 24, 2018, and, Ser. No. 62/492,971, entitled: Device Creating Dense Cloud Particles Spray/Mist, filed on May 2, 2017, the disclosures of both of these provisional patent applications are is incorporated by reference in their entirety herein.

TECHNICAL FIELD

The present invention is directed to systems and methods for maintain sanitary conditions bathroom receptacles, such as toilets.

BACKGROUND

As all modern domestic and commercial buildings include toilets, sanitation has improved vastly. However, simply flushing a toilet still allows for the escape of odors, water and contaminants, from the toilet bowl. This makes for an uncomfortable situation for a user of the toilet.

SUMMARY

The present invention is directed to methods and systems for sanitation, and in particular, to methods and systems for controlling contaminates and other infectious materials from leaving a toilet bowl upon being flushed.

The present invention is directed to a sanitation device for a toilet bowl. The sanitation device comprises: a toilet flush detection sensor; and, a sprayer in electronic communication with the toilet flush sensor, the sprayer configured for spraying a substance across the opening of the toilet bowl to create a barrier for contaminants from leaving the toilet bowl.

Optionally, the sanitation device additionally comprises: a holder for connecting to the toilet bowl and supporting the toilet flush detection sensor and the sprayer.

Optionally, the sprayer includes: a chamber enveloping: 1) a valved canister including an aerosol including the substance; and, 2) an actuator for moving the valve so as to release the aerosol from the canister, in response to the toilet flush detection sensor detecting a toilet flush.

Optionally, the substance includes a sanitizer.

Optionally, the sprayer additionally comprises: a nozzle from which aerosol is released from the sprayer; and, a conduit in communication with the chamber and the nozzle.

Optionally, the toilet flush detection sensor detects one or more of: water associated with the toilet flush and a sound of a toilet flush.

Optionally, the sanitation device additionally comprises: a controller in electronic communication with the toilet flush detection sensor and the actuator, the controller configured for controlling the actuator to open the valve for a predetermined amount of time, in response to the toilet flush detection sensor detecting a toilet flush.

Optionally, the holder is configured for attaching to the rim of the toilet bowl.

Optionally, the controller includes processors.

Optionally, the sanitation device additionally comprises: an ultra-violet (UV) light source in electronic communication with the controller for activating for a predetermined time, in response to the toilet flush detection sensor detecting a toilet flush.

Optionally, the sanitation device additionally comprises a fan unit in electronic communication with the controller for activating for a predetermined time, in response to the toilet flush detection sensor detecting a toilet flush.

Optionally, the sanitation device additionally comprises a power source in electronic communication with the controller.

Embodiments of the present invention are directed to a sanitation device for a toilet bowl. The sanitation device comprises: a toilet flush detection sensor; and, an ultraviolet (UV) light source in electronic communication with the toilet flush sensor, the UV light source for spraying a sanitizer across the opening of the toilet bowl to create a barrier for contaminants from leaving the toilet bowl.

Embodiments of the present invention are directed to a sanitation device for a toilet bowl. The sanitation device comprises: a toilet flush detection sensor; and, a fan unit in electronic communication with the toilet flush sensor, the fan unit for creating airflow in the toilet bowl, preventing upward airflow from the toilet bowl.

Embodiments of the present invention are directed to method for sanitizing a toilet bowl. The method comprises: detecting a toilet flush by a toilet flush detection sensor; and, responding to the detection of the toilet flush by causing a sprayer to release a substance across the opening of the toilet bowl, to create a barrier for contaminants from leaving the toilet bowl.

Optionally, the method is such that the spraying is substantially perpendicular to a vertical axis of the toilet bowl.

Optionally, the method is such that the substance includes one or more of a sanitizer and a decontaminant.

Optionally, the method additionally comprises: activating an ultraviolet (UV) light source in response to the detection of the toilet flush.

Optionally, the method additionally comprises: activating a fan in response to the detection of the toilet flush.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. In the drawings.

DETAILED DESCRIPTION OF THE INVENTION

The present invention is directed to methods and systems for sanitation, and in particular, to methods and systems for preventing and controlling contaminates and other infectious materials from leaving a toilet bowl upon being flushed. There is provided a spray of material, emitted from a device, which propels the material across the toilet bow, covering the open plane of the toilet bowl, to keep contaminates and other infectious materials from leaving the toilet bowl. The spray is emitted when the flush of the toilet is detected, the spray serving to block particles of a waste plume created by the flush water.

Figure 1A:
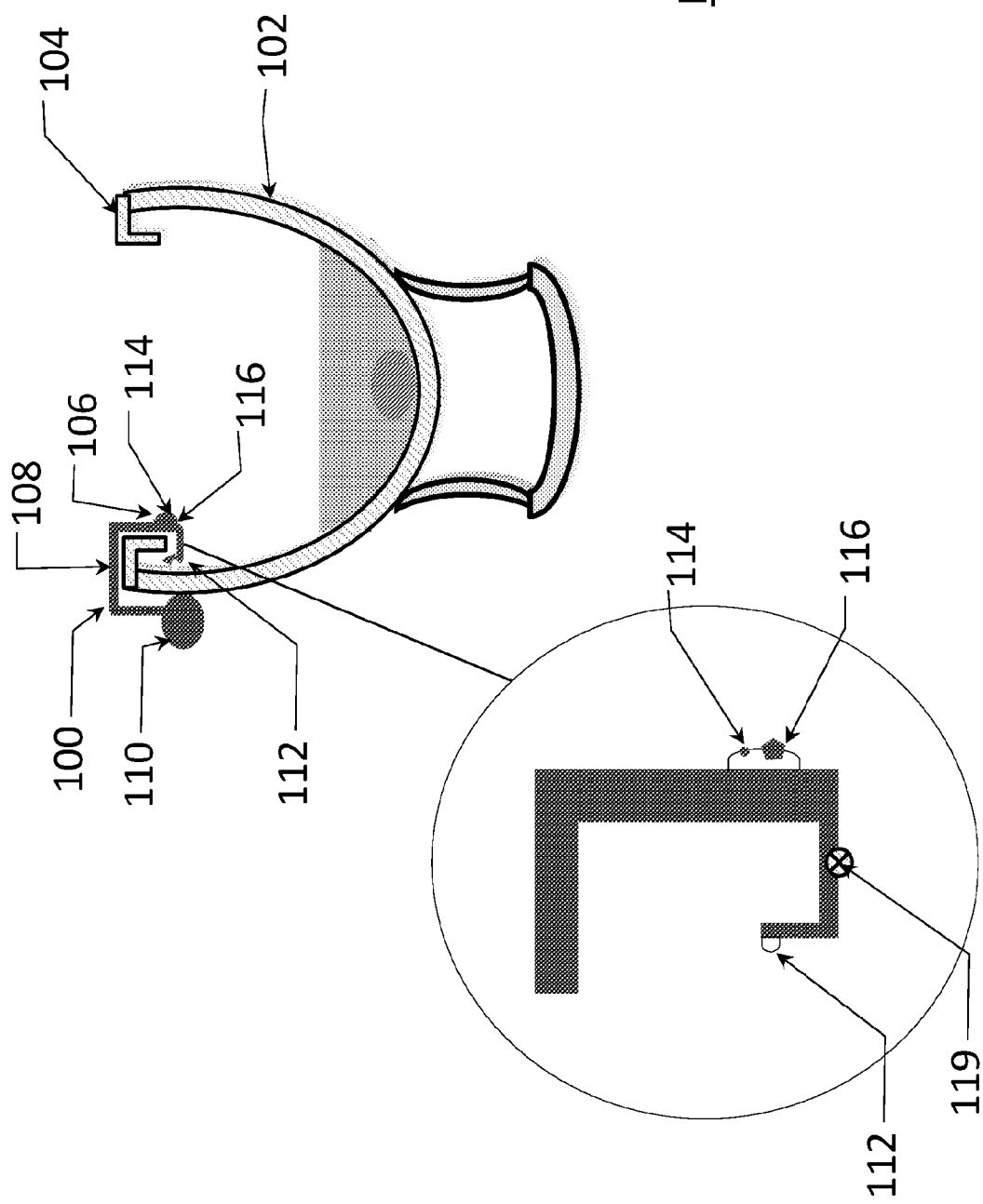
FIG. 1A is a sectional view of the apparatus of the invention in an exemplary operation on a toilet.

FIG. 1A shows an apparatus 100 which attaches to a toilet bowl 102, proximate to the rim 104. The apparatus 100 includes a hook member or holder 106, which sits, for example, in the toilet bowl 102, which connects to a conduit support 108 spanning the rim 104, which in turn supports a sprayer 100x. The sprayer 110x includes, for example, a chamber 110, which holds a valved canister 128 (which contains a substance, such as a chemical agent, e.g., sanitizer, in an aerosol form or other aerosol) and an actuation system therefor, in an enveloping arrangement. The sprayer 100x also includes a conduit 130, which extends from the chamber to a nozzle 116, through which the agent is released into the toilet bowl. The hook member 106, conduit support 108 and chamber 110, are, for example of flexible materials so as to frictionally engage the apparatus 100 to the rim 104.

Figure 1B:
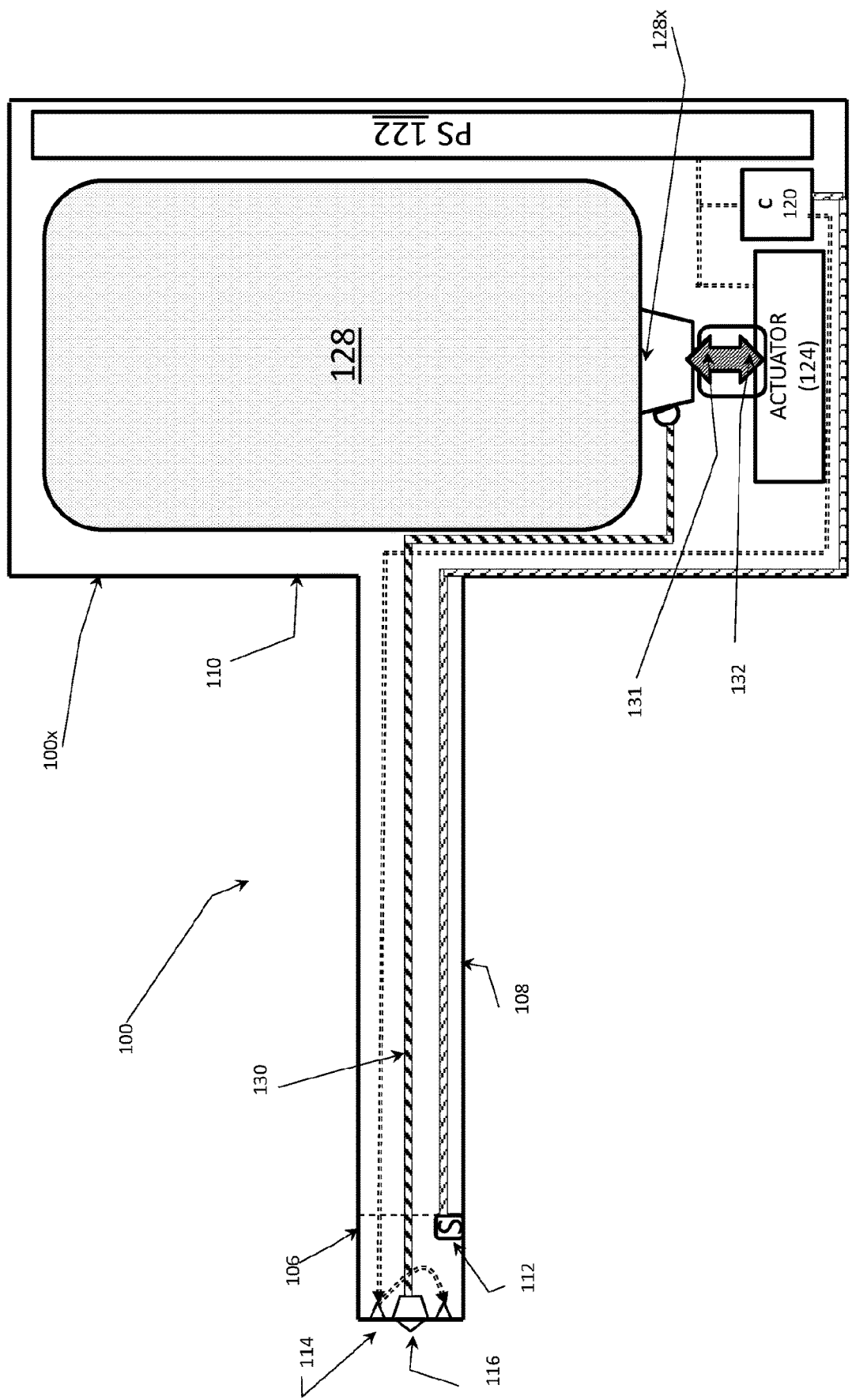
FIG. 1B is a top view of the apparatus of FIG. 1A.

Turning also to FIG. 1B, the hook member 106 supports a sensor (S) 112, which is for example, a flush detector. This sensor 112 is, for example, a water detection sensor, or alternately, is an electrical sensor, in a water tight package, which detects the toilet flush by sounds, vibrations and the like. The sensor 112, for example, sits external to the hook member 106, without touching the rim 104, so as to receive water flow from the flush. The sensor 112 links (electrically and or in data communication) to the controller 120 for indicating that a flush has been detected.

An Ultraviolet (UV) light source 114 is also supported by the hook member 106 for providing sanitizing UV light to the toilet bowl 102, when activated, for example, by the toilet flush. The hook member 106 also supports a nozzle 116, which is, for example, adjustable (allowing the user to control the trajectory of the spray), and designed to direct the chemical agent laterally, as a spray, for example, in a cone-like shape, to cover the open area of the toilet bowl 102, negating any upward spray or discharge from the flushing water, while keeping the waste plume in the toilet bowl 102. The propulsion of the chemical agent is at a force and duration to keep material being flushed, within the toilet bowl 102, such that the flush is completed without any material leaving the toilet bowl.

Figure 6:
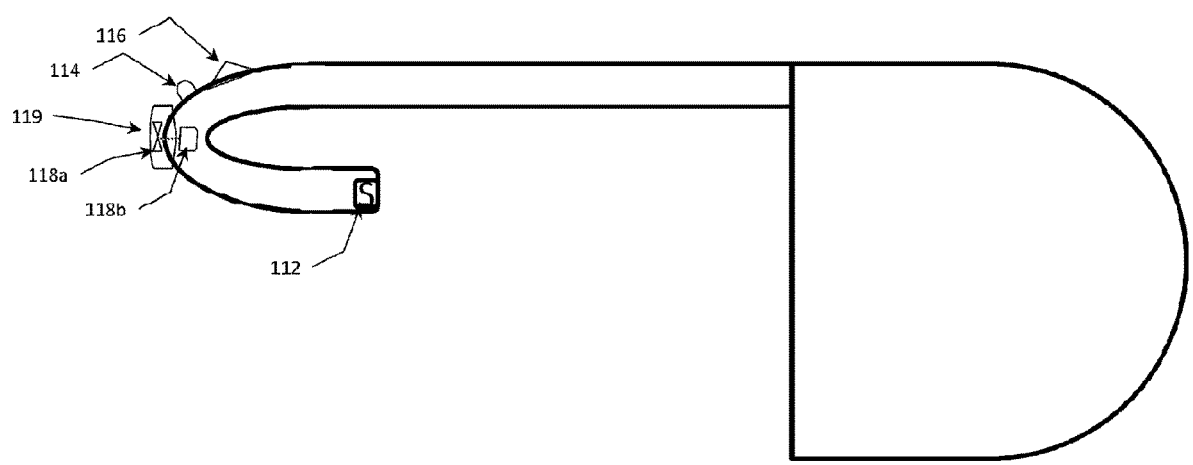

A fan 118a, and a motor 118b for its activation and action, collective forming a fan unit 119, is also supported on the hook member 106, in a position such that when activated, by the controller (C), creates an air movement in the bowl, to counter outward motion of the air and contaminants. This air movement from the fan 118a facilitates the air to move in a rotational pattern horizontally in the bowl 102, and perpendicular or substantially perpendicular to the vertical axis of the bowl 102. The fan 118a is powered by the motor 118b, which is activated by the controller 120. Activation of the fan 118a is, for example, for a predetermined time to control airflow after flushing for creating airflow in the toilet bowl, preventing outward (upward) airflow from the toilet bowl. The fan unit 119 is shown in detail in FIG. 6.

The chamber 110, for example, includes a controller (C) 120, which is linked to the sensor 112, UV light source 114, as well as a power source (PS) 122 (e.g., a battery), and an actuator 124, for example, a solenoid, which moves based on signals from the controller 120. The solenoid 124 abuts a canister 128, which is the source of a chemical agent, under pressure. The movement of the actuator 124, for example, the solenoid, causes emission of the chemical agent out of the canister 128, through the conduit 130 and into the toilet bowl 102 via the nozzle 116. Additionally, the chamber 110, for example, is anchored the external surface of the toilet bowl 102, by adhesives and other suitable fasteners.

The chemical agent, for example, is in the form of a spray, such as an aerosol. This spray typically includes sanitizers, such as disinfectants, antibacterial agents, and may also include scents, perfumes and the like. The spray may also include bleaches, for sanitizing and cleaning the toilet bowl during and after the flush. The spray, as released from the nozzle 116 is, for example, of a density suitable to retain any upward discharges of water or contaminants from the flush, within the toilet bowl 102.

Figure 2:
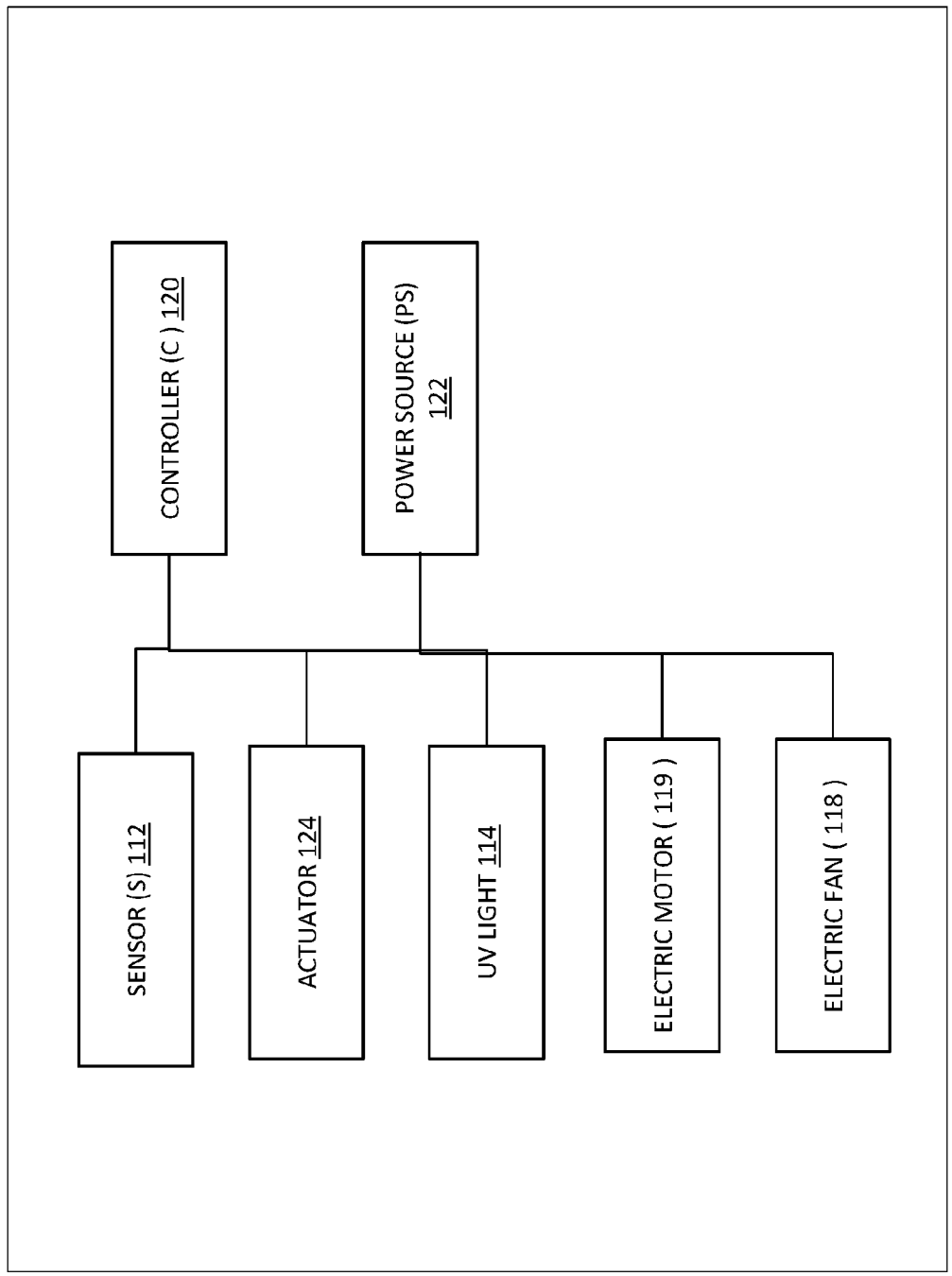
FIG. 2 is a block diagram of an electrical schematic of the system of the apparatus of FIGS. 1A and 1B.

FIG. 2 shows an electrical signal block diagram or schematic of the system of the apparatus 100. All of the aforementioned components are linked to each other, either directly or indirectly and by wired and/or wireless links. By "linked", it is meant electrical and/or data communication.

Figure 4:
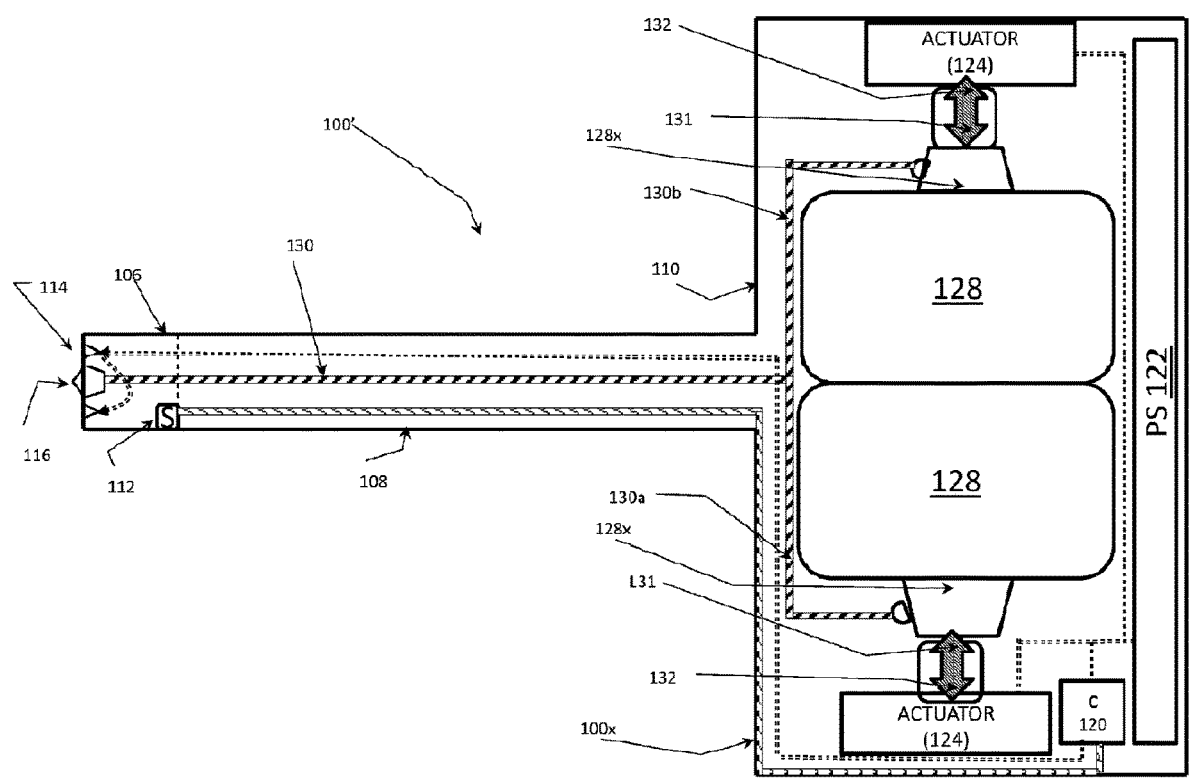
FIG. 4 is a diagram of an alternate embodiment in accordance with the present invention.
Figure 5:
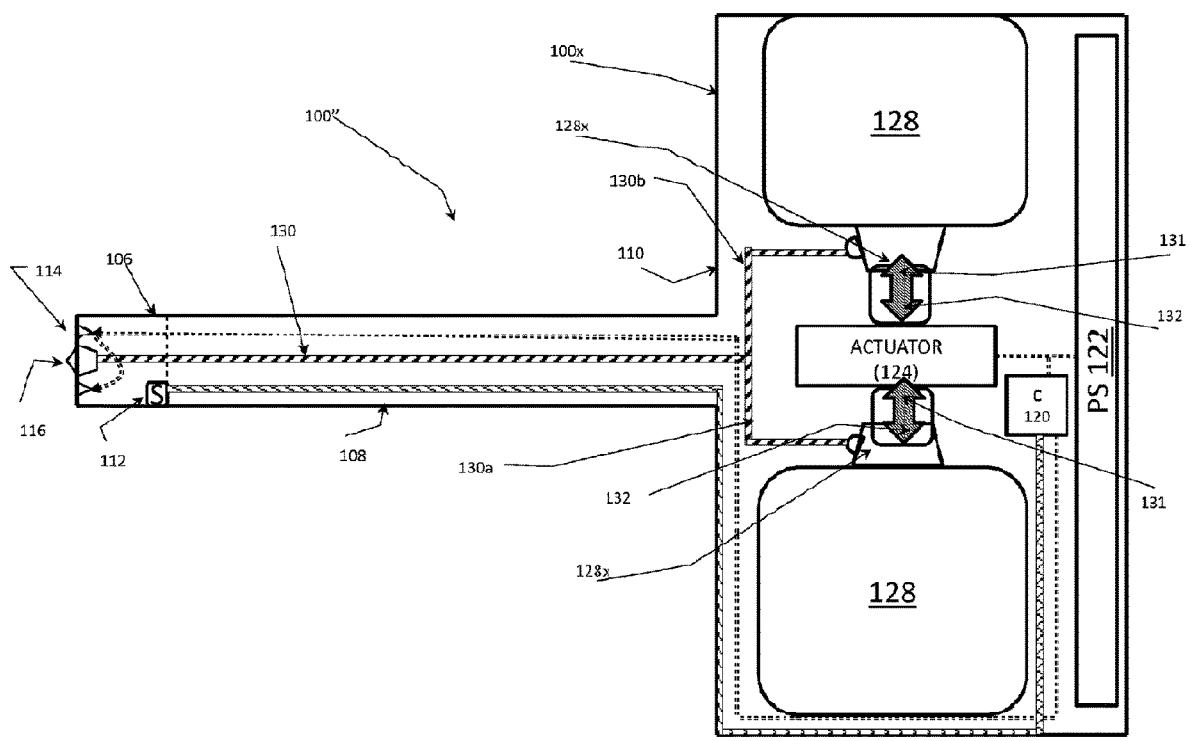
FIG. 5 is a diagram of another alternate embodiment in accordance with the present invention; and, FIG. 6 is a cross sectional view the hook member of the apparatus including the fan and motor, in accordance with the present invention.

The controller 120 is, for example, processor based and is programmed to receive signals from the sensor 112. These signals from the sensor 112 typically are based on an indication of the flush of the toilet. The signals from the sensor 112 are processed to cause activation of the UV light source 114 and/or movement of the actuator 124 (i.e., solenoid) (or actuators 124 of apparatus 100' of FIG. 4). For example, when the actuator 124 is the solenoid as shown, the solenoid moves in the direction of the arrow 131 (and upon completion of the actuator 124 returns to its previous position in accordance with the arrow 132), to cause emission of the chemical agent from the canister 128, by opening a valve 128x of the canister 128, for example, for a predetermined time, for emission of the spray through the nozzle 116, into the toilet bowl 102. By opening the valve 128x for the predetermined time, a sufficient amount of spray is released to create a barrier for contaminants from leaving the toilet bowl.

Attention is now directed to FIGS. 3A-3G which show the apparatus 100 of the invention in an example operation.

Figure 3:
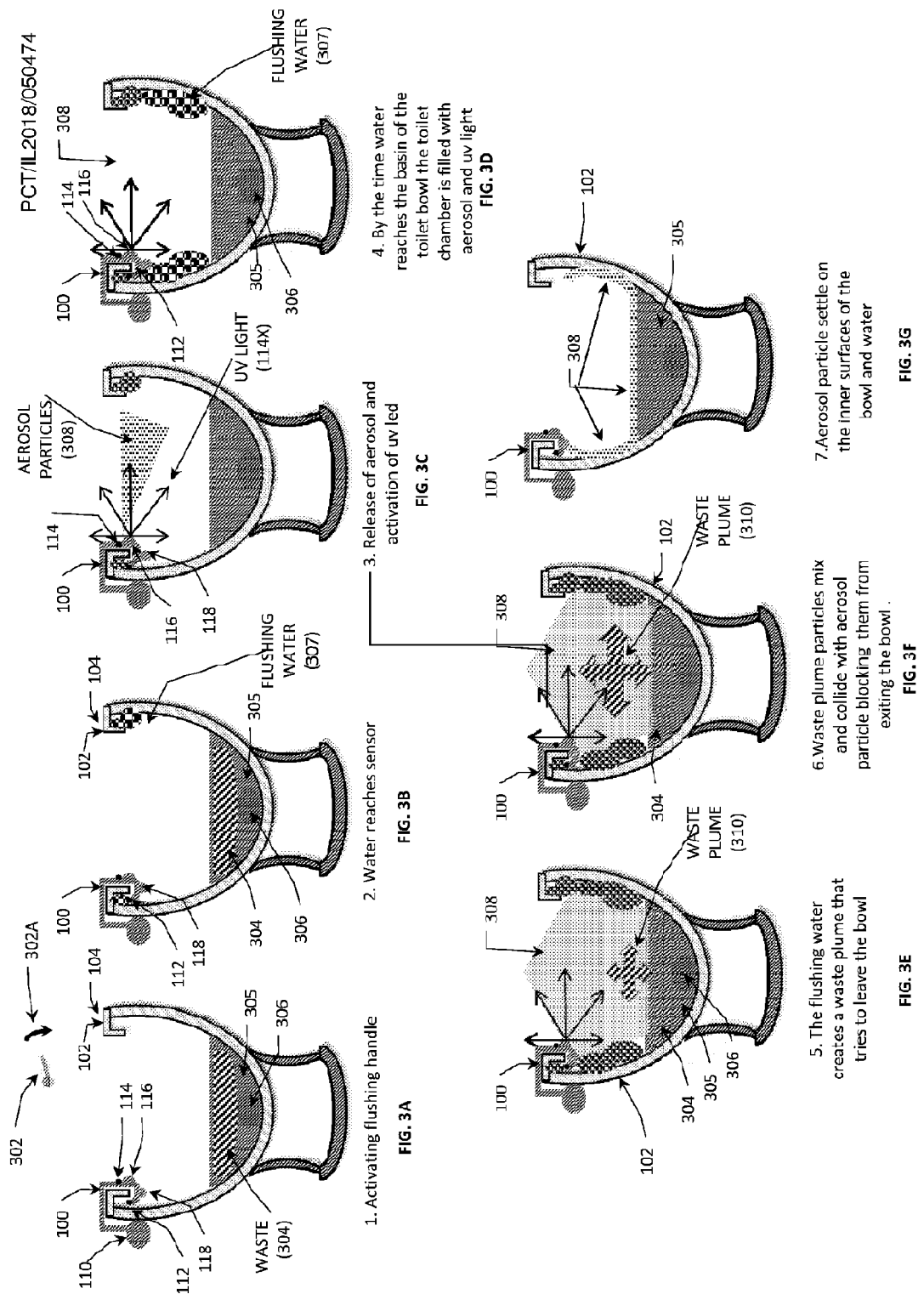
FIGS. 3A-3G are diagrams detailing an example operation of an embodiment of the invention.

Initially at FIG. 3A, the apparatus 100 is attached to a toilet bowl 102 at the rim, in a frictional engagement. The toilet includes a flushing handle 302, which when activated, for example, by being pulled downward (as illustrated by arrow 302a), releases water into the toilet bowl so as to flush the waste material 304, sitting in water 305, down an exit pipe 306 connected to the toilet bowl 102.

In FIG. 3B, the water 307, released by the flush has reached the sensor 112 of the apparatus 100. With the sensor 112 having detected the flush, via the flush water 307, the sensor 112 signals the controller 120. The controller 120 signals the UV light 114 to activate 114x, as well as the actuator 124, causing the release of an aerosol spray 308, e.g., sanitizer, of chemical agent, through the nozzle 116, from the canister 128 (via the conduit 130), as shown in FIG. 3C.

The aerosol spray 308 is released from the canister 128 and through the nozzle 116, for example, at a trajectory (across the toilet bowl) to remain in the toilet bowl 102, and for a time, such that a sufficient amount of the spray 308 fills the toilet bowl 102 (e.g., across the opening of the toilet bowl 102), as shown in FIG. 3D. Also in FIG. 3D, the UV light 114 is also activated or ON for a sufficient or predetermined time to have a germicidal and sanitizing effect.

In FIG. 3E the flushing water creates turbulence which results in a waste plume 310. This waste plume 310 expands outward and moves upward in the toilet bowl 102. In FIG. 3F, the particles of the waste plume 310 collide and mix with the particles of the aerosol spray 308. The particles of the aerosol spray 308, cover the open volume of the toilet bowl 102, to block the waste plume 310 from leaving the toilet bowl 102. With the waste plume 310 blocked, the particles of the aerosol spray 308 settle on the inner surfaces of the toilet bowl 102 and the water 305.

FIG. 4 shows an alternative apparatus 100' similar to the apparatus 100 of FIGS. 1A, 1B and 2, except that there are duel actuators 124, oppositely disposed from each other in the chamber 110. Each actuator 124 is linked to the controller 120, and once an activation signal is received, a canister 128 is activated, opening a valve 128*x*, releasing spray through the conduit 130, via feeder conduits 130*a*, 130*b*. The controller 120 and actuators 124 are arranged such that the actuators can operate together, e.g., simultaneously, or separately, and if separately for the same or different spraying times.

FIG. 5 shows an alternative apparatus 100" similar to the apparatus 100 of FIGS. 1A, 1B and 2, and 100' of FIG. 4, except that that there are single actuators 124, between oppositely disposed release mechanisms 124*a*, of the respective canisters 128. The actuator 124 is linked to the controller 120, and once an activation signal is received, the actuator 124 moves (as per double headed arrows 131, 132) such that one of the canisters 128 is activated, releasing spray through the conduit 130, via the respective feeder conduit 130*a*, 130*b*. The controller 120 and actuator 124 are such that actuation alternates between canisters 128 over a predetermined time period or interval.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. A device for treating a waste plume in a toilet bowl comprising: a toilet flush detection sensor; and, a sprayer in electronic communication with the toilet flush sensor, the sprayer including a nozzle configured to spray a substance, to substantially fill the opening of the toilet bowl, the substance of a density to create a downward flowing barrier for contaminants from a waste plume from leaving the toilet bowl, the spraying in instantaneous response to the toilet flush detection sensor detecting the toilet flush.

2. The device of claim 1, additionally comprising: a holder for connecting to the toilet bowl and supporting the toilet flush detection sensor and the sprayer.

3. The device of claim 1, wherein the sprayer includes: a chamber enveloping: 1) a valved canister including the substance; and, 2) an actuator for controlling the valve so as to release the substance from the canister, in response to the toilet flush detection sensor detecting a toilet flush.

4. The device of claim 3, wherein the substance includes a sanitizer.

5. The device of claim 3, wherein the nozzle is additionally configured for atomizing the substance.

6. The device of claim 3, wherein the toilet flush detection sensor detects one or more of: water associated with the toilet flush and a sound of a toilet flush.

7. The device of claim 3, additionally comprising: a controller in electronic communication with the toilet flush detection sensor and the actuator, the controller configured for controlling the actuator to control the valve for a predetermined amount of time, in response to the toilet flush detection sensor detecting a toilet flush.

8. The device of claim 2, wherein the holder is configured for attaching to the rim of the toilet bowl.

9. The device of claim 7, wherein the controller includes at least one processor.

10. The device of claim 7, additionally comprising a ultra-violet (UV) light source in electronic communication with the controller for instantaneously activating for a predetermined time, in response to the toilet flush detection sensor detecting a toilet flush.

11. The device of claim 7, additionally comprising a fan unit in electronic communication with the controller for instantaneously activating for a predetermined time, in response to the toilet flush detection sensor detecting a toilet flush.

12. The device of claim 7, additionally comprising a power source in electronic communication with the controller.

13. A device for treating a waste plume in a toilet bowl comprising: a toilet flush detection sensor; a sprayer in electronic communication with the toilet flush sensor, the sprayer including a nozzle configured to spray a substance, to substantially fill the opening of the toilet bowl, the substance of a density to create a downward flowing barrier for contaminants from a waste plume from leaving the toilet bowl, the spraying in instantaneous response to the toilet flush detection sensor detecting the toilet flush; and, an ultraviolet (UV) light source in electronic communication with the toilet flush sensor, and configured for activating contemporaneously with the sprayer having been activated.

14. A method for treating a waste plume in a toilet bowl, comprising: detecting a toilet flush by a toilet flush detection sensor; and, responding to the detection of the toilet flush by causing a sprayer including a nozzle to instantaneously spray a substance to substantially fill the opening of the toilet bowl, the substance of a density to create a downward flowing barrier for contaminants from the waste plume from leaving the toilet bowl.

15. The method of claim 14, wherein the substance includes one or more of a sanitizer, a decontaminant, and a perfume.

16. The method of claim 14, additionally comprising: activating an ultraviolet (UV) light source in response to the detection of the toilet flush.

17. The method of claim 14, additionally comprising: activating a fan in response to the detection of the toilet flush.

18. The device of claim 5, wherein the sprayer additionally comprises: a conduit in communication with the chamber and the nozzle.

19. The device of claim 18, wherein the nozzle is configured in a position such that the spraying of the substance substantially fills the opening of the toilet bowl.

20. The device of claim 18, wherein the nozzle is movable between a plurality of positions such that the spraying of the substance substantially fills the opening of the toilet bowl.

21. The device of claim 1, wherein the sprayer is configured for operating for a predetermined time such that the substance is sprayed for a predetermined time.

22. A device for treating a waste plume in a toilet bowl comprising: a toilet flush detection sensor; and, a sprayer in electronic communication with the toilet flush detection sensor, the sprayer configured for instantaneous activation upon the toilet flush detection sensor detecting water flushing in the toilet bowl, the instantaneous activation of the sprayer causing the release of a substance into the toilet bowl opening, the substance of a density to create a downward flowing barrier for contaminants from a waste plume from leaving the toilet bowl.

23. A device for treating a waste plume in a toilet bowl comprising: a toilet flush detection sensor; a sprayer in electronic communication with the toilet flush sensor, the sprayer including a nozzle configured to spray a substance for a predetermined time, to substantially fill the opening of the toilet bowl, the substance of a density to create a downward flowing barrier for contaminants from a waste plume 22 from leaving the toilet bowl, the spraying in instantaneous response to the toilet flush detection sensor detecting the toilet flush; and, an ultraviolet (UV) light source in electronic communication with the toilet flush sensor, and configured for activating during the predetermined time.

* * * * *